United States Patent [19]
Mariant et al.

[11] Patent Number: 6,143,007
[45] Date of Patent: Nov. 7, 2000

[54] METHOD FOR MAKING AN OCCLUSIVE DEVICE

[75] Inventors: Michael J. Mariant, San Jose; Gene Samson, Milpitas, both of Calif.

[73] Assignee: Target Therapeutics, Inc., Fremont, Calif.

[21] Appl. No.: 08/431,360

[22] Filed: Apr. 28, 1995

[51] Int. Cl.$^7$ .................................................. A61B 17/00
[52] U.S. Cl. ........................................ 606/151; 606/191
[58] Field of Search .................................. 606/151, 191, 606/213

[56] References Cited

U.S. PATENT DOCUMENTS

| | | |
|---|---|---|
| 3,687,129 | 8/1972 | Nuwayser . |
| 4,820,298 | 4/1989 | Leveen et al. . |
| 4,994,069 | 2/1991 | Ritchart et al. . |
| 5,084,065 | 1/1992 | Weldon et al. . |
| 5,122,136 | 6/1992 | Guglielmi et al. . |
| 5,256,146 | 10/1993 | Ensminger et al. . |
| 5,261,916 | 11/1993 | Engelson . |
| 5,282,846 | 2/1994 | Schmitt . |
| 5,304,194 | 4/1994 | Chee et al. . |
| 5,304,195 | 4/1994 | Twyford, Jr. et al. . |
| 5,312,415 | 5/1994 | Palermo . |
| 5,350,397 | 9/1994 | Palermo et al. . |
| 5,354,295 | 10/1994 | Guglielmi et al. . |
| 5,382,259 | 1/1995 | Phelps et al. . |
| 5,382,260 | 1/1995 | Dormandy, Jr. et al. . |

OTHER PUBLICATIONS

Castaneda–Zuniga et al., "A new device for the safe delivery of stainless steel coils" *Radiology* (1980) 136:230–231.

*Primary Examiner*—Michael H. Thaler
*Attorney, Agent, or Firm*—Morrison & Foerster LLP

[57] ABSTRACT

This invention is a surgical device. In particular, it is an implant which may be used to occlude vascular lumens, arteries, veins, aneurysms, vascular malformations, arteriovenous fistulas, or other cavities and lumens within a mammalian body. It is typically a substrate coil or braid to which a number of fibers have been secured using heat.

6 Claims, 4 Drawing Sheets

METHOD FOR MAKING AN OCCLUSIVE DEVICE

FIELD OF THE INVENTION

This invention is a surgical device. In particular, it is an implant which may be used to occlude vascular lumens, arteries, veins, aneurysms, vascular malformations, arteriovenous fistulas, or other cavities and lumens within a mammalian body. It is typically a substrate coil or braid to which a number of fibers have been secured using heat.

BACKGROUND OF THE INVENTION

This invention is an occlusive device, and typically includes a substrate, often a helical metal coil, and a multiplicity of fibers incorporated therewith for enhancing a tissue-ingrowth response for occlusion.

We use the term "occlusive devices" to encompass devices for occluding vascular lumens as well as any other body cavities requiring occlusion to carry out a medical treatment. We use the term "vaso-occlusion devices" to encompass devices used in endovascular applications, such as in occluding veins, arteries, fistulas, or aneurysms. Although the invention is described largely in terms of vaso-occlusion devices, we intend the present invention to include the wider scope of occlusion devices.

Vaso-occlusion devices of the prior art have been associated with two pertinent limitations.

First, fibers for enhancing the thrombogenicity of vaso-occlusion devices must be securely attached to an underlying substrate, usually a coil, of the device. Without being secured, detachment of the fibers from the substrate coil could cause embolization at some remote, undesired site in the vasculature.

Second, vaso-occlusion devices are re-deployed through conduit delivery tubes (e.g., catheters or sheaths), often to sites in distant tortuous portions of the anatomy. Such delivery tubes often fit closely over the occlusive device. Such a fit may become tight upon any ovalization of the delivery tube in tight bends of a distal tortuous lumen. The presence of fibers extending from the vasoocclusive device and the orientation that those fibers take can add a significant frictional component during the deployment of the device through the delivery tube. Friction due to the fibers becomes more of a problem when larger coils are employed and when distal, tortuous anatomy must be negotiated.

The shape of the occlusive devices determines the overall profile of the delivery system and resultant negotiability of the system in the anatomy. The delivery system profile, in turn, affects patient morbidity. Thus, larger coil substrates present a more difficult problem in terms of accommodating fibers in the intraluminal space with the delivery conduit tube. One way of meeting such a challenge is shown in Castaneda-Zuniga, et al., in "A New Device for the Safe Delivery of Stainless Steel Coils," Radiology 136:230–231. This document suggests that delivery of coils to larger arteries requires large-bore TEFLON-lined catheters in order to decrease the friction that occurs as the coil is introduced.

Where tortuous anatomy must be negotiated, the conduit delivery tube lumen often assumes an oval cross section (i.e., it becomes "ovalized") within a turn and effectively narrows the lumen. Here, as well, the ability to accommodate the thrombogenic fibers on substrate coils of occlusion devices becomes more limited.

The following documents are typical descriptions of various implantable devices having attached fibers.

U.S. Pat. No. 5,256,146, to Ensminger et al., discloses an implantable vascular catheterization system for maintaining the tip of an implanted catheter at a desired position within a blood vessel. The disclosure describes a device having an anchoring filament with "clotting means" attached. These clotting means may be numerous filaments of a textile material or 'fuzz' intended to cause the blood vessel in the anchoring area become occluded due to blood clotting. No technique for attaching the fibers is shown nor are any particular orientation of the fibers described.

U.S. Pat. No. 5,382,260, to Dormandy, teaches an embolization device made up of a metal coil with fibers. Each group of fibers has an intermediate portion looped about one central turn of the coil. The ends of the fibers extend interiorly of the coil and outwardly of the coil through the spaces between two adjacent turns that are adjacent the central turn. The ends of the fibers are free to move. The loop serves as the sole means for retaining the group of fibers on the coil.

The ends of the group of fibers extend radially from the coil at the same position. They are said to be spaced extremely close along the longitudinal axis, with multiple fibers bundles spaced a "suitable distance" apart. This configuration focuses a frictional component on one side of the catheter. The closeness and overall quantity of fibers that can be placed on the coil is therefore limited by the increased friction from concentrated fiber bundles in the intraluminal space on substantially one side of the coil. The "suitable distance" that multiple fibers must be spaced apart is largely determined by the frictional resistance limitation through the delivery tube attributable to the fibers in the disclosed orientation.

U.S. Pat. No. 5,304,194 to Chee, the disclosure from which is herein incorporated by reference, discloses a vaso-occlusive device having a metal coil with at least one fibrous element attached to its proximal end. The fibrous element extends in a sinusoidal wave that loops about individual windings at intervals spaced along the axis of the coil. Chee teaches that a method for attaching the fibrous element is tying a knot to secure the end of the fiber onto the coil. Chee further teaches that knotting at the ends is desirable, but not essential, since threading of the loops about the windings is sufficient to anchor the bundle to the coil.

Since Chee teaches the use of loops of fiber extending from the coil substrate having successive loops oriented longitudinally along the substrate coil, the fibers of the have a relatively constant radial aspect on the coil substrate.

Although Chee also teaches the use of fibers on opposite radial sides of the coil, a different fiber is present on each of the two opposing radial positions. Also, the fibers of this embodiment form loops external to the coil. The embodiment requires looping the fiber on one side of the coil substantially on the same coil windings as where the fiber on the opposite coil side is looped to avoid effectively tying the opposite loop down upon the coil.

U.S. Pat. No. 4,820,298, to Leveen et al., discloses a device for sealing off the dilated portion of a vascular aneurysm. Leveen et al discloses a flexible tubular body formed from a medical thermoplastic in the form of a helix. The helical loops of the flexible tubular body are connected to strands which extend into the space defined by each coil of the helix to allow clot formation and ingrowth of tissue. Leveen teaches interfacing the strands with the coils by mounting or integrally forming them with the tubular substrate body. Such mounting or integral forming is said to be accomplished through the use of sonic welding or adhesives.

U.S. Pat. No. 5,382,259, to Phelps, teaches a vasoocclusion coil onto which a fibrous, woven, or braided tubular covering or element is placed co-axially to an underlying substrate by melting, fusing, or gluing the covering to at least one end of the substrate. The substrate is typically a braid or coil. This device is described as presenting a high ratio of fibrous material to metallic material and as being easily placed within the body's vasculature.

U.S. Pat. No. 3,687,129, to Nuwayser, teaches a male contraceptive device comprising a plug with a very fine layer of flock or coating of fabric on its outer walls. Nuwayser teaches that the fabric web may be heat bonded in mats to a sheet of polymer. The polymer is heated with gradually rising temperature until the polymer surface is softened, and the fabric is then impressed on the soft surface with an embossed press to ensure the formation of cell-entrapping loops. The disclosure states that the bonding technique is enhanced by using a substrate polymer whose melting point is lower than the fabric material.

The device described in Nuwayser is a hollow plug said to be suitable as a vas deferens occluding device. The device has a fabric lining on its interior surface similar to that fabric taught for the outer surface. Bonding techniques taught for the outer fabric are also taught for the interior fabric.

None of the cited references teaches a device for occluding body lumens or cavities having fibers secured to a substrate with free fiber ends extending outwardly from the occlusion device at radially spaced locations on the substrate when deployed in-vivo where the free ends orient longitudinally in the intra-luminal space when the device is delivered through a delivery sheath and consequently parallel to the friction plane to enhance co-axial delivery.

None of the references teach heating an interface between thrombogenic fibers and vaso-occlusive substrates to cause localized deformation in at least one of said substrate or fibers, securing the fibers to the substrate in a desired orientation for enhanced thrombogenesis and co-axial delivery to distal anatomy.

SUMMARY OF THE INVENTION

The invention is a device for occluding body lumens or cavities. The device is made up of a substrate, preferably a coil, adapted for placement within a lumen or cavity, and a plurality of fibers that extend outwardly from the substrate at an interface with the substrate. The substrate, if a helically wound coil, may be a.) one which is simply pushed from a delivery catheter or b.) may be mechanically or independently detachable from the associated pusher or c.) may be detachable from the pusher by the use of a sacrificial electrolysis-susceptible joint between the pusher and substrate. The fibers are secured to the substrate at the interface by heating the interface to cause a material deformation in at least one of the fibers or substrate at the interface, said deformation preventing detachment.

DESCRIPTION OF THE INVENTION

Figures 1, 2:
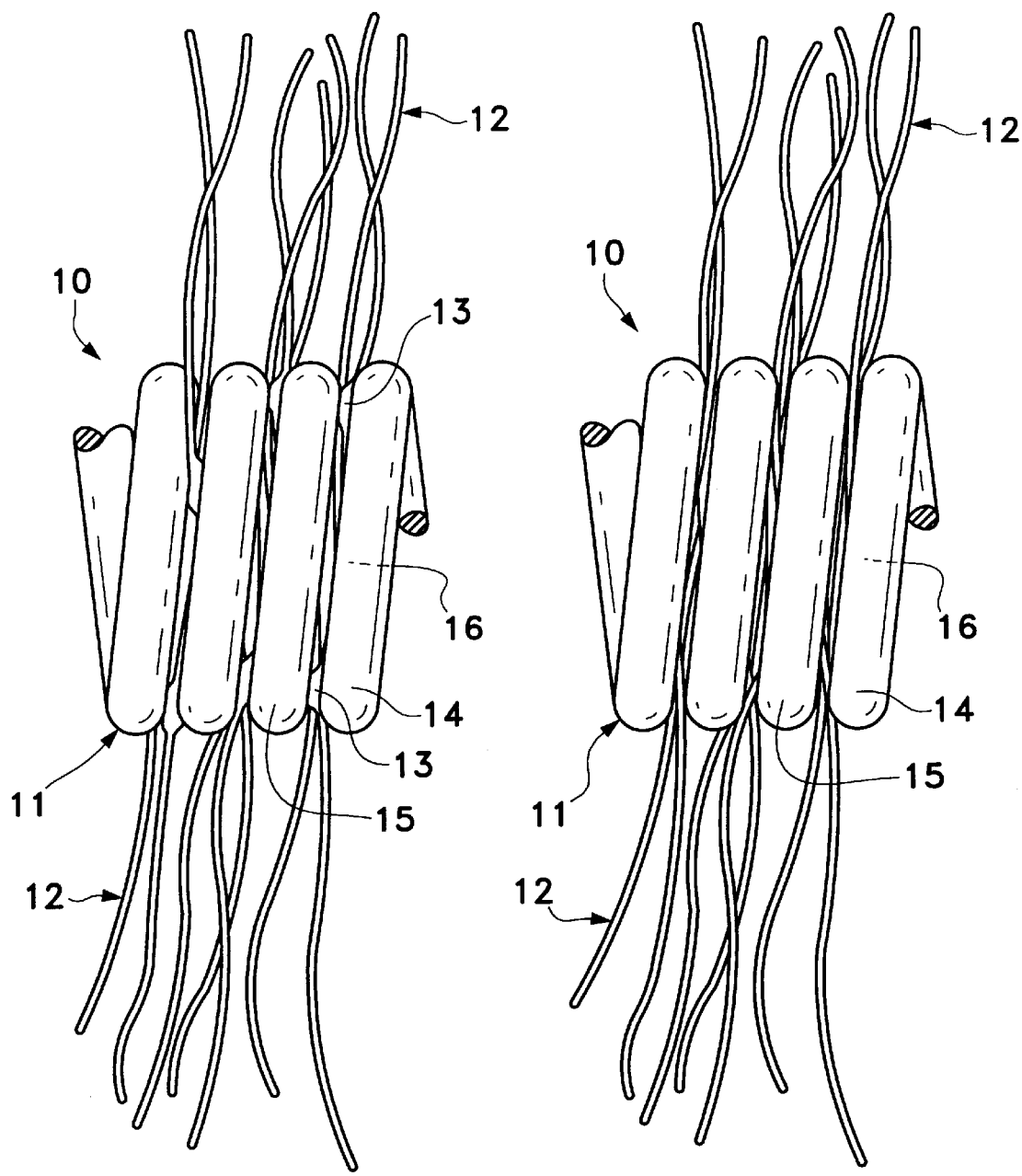
FIG. 1 shows a side view portion of the occlusion device after using heat to secure fibers to a substrate coil.
FIG. 2 shows a side view portion of the occlusion device before heating the interface of a substrate coil and fibers.

This invention is a medical device, having a substrate and a plurality of fibers as two principal components, typically made using heat to secure the two components together. FIG. 1 depicts a preferred embodiment of the invention. The substrate 11 is shown as a helically wound coil. It has fibers 12 which extend radially outward from the coil. The fibers 12 have a heat deformation region 13 shown at the various interfaces between fiber 12 and substrate 11, e.g., between coil windings 14 and 15. Because the deformation 13 is thermally formed using the procedure described elsewhere, the deformation 13 secures the fibers 12 to substrate 11. When the fiber is a thermoplastic, contains a thermoplastic, or is coated with a thermoplastic, the softening or melting of the polymer in the fiber as is produced using the noted thermal procedures promotes adhesion of the fiber to the substrate.

Although the invention may involve deformation of either or both of the fibers 12 and/or substrate 11, for ease and economy of description, most of the further embodiments of the invention described below utilize a metal helical coil as the exempletive substrate. In this way the heat deformation 13 is largely isolated in the preferred thermoplastic polymeric fibers. Other substrates, e.g., braids or tubing or combinations of these with coils are included within the scope of the invention.

FIG. 2 shows the device of FIG. 1 before being heated by one of the preferred methods to secure the fibers 12 to the substrate coil 11. FIG. 2 shows fibers 12 threaded between windings 14 and 15 of coil 11 before heating.

The substrate coils 11 are typically made of a metal such as platinum, tungsten, gold, stainless steel, or of alloys such as tungsten and platinum. A tungsten-platinum alloy is preferred because of its strength and toughness. The material desirably is radiopaque and the diameter of the wire will usually be in the range of 0.0005 to 0.010 inches. The coil 11 has a multiplicity of individual windings, as shown by example at 14 and 15, to form a helix with an internal lumen 16 typically having an inner diameter from 0.0015 to 0.040 inches, preferably being about 0.009 inches. The axial length of the coil will usually be in the range of 0.2 to 100 cm, more usually 0.2 to 40 cm and the diameter of the coil will normally be 0.006 to 0.080 inches. For most neurological uses the coil diameter may be in the range of 0.010 to 0.040 inches. The coil will typically have about 5 to 70 windings per cm, more typically about 10 to 40 windings per cm.

Coils having an O.D. from 0.020 to 0.080 inches, preferably 0.020 to 0.060 inches, are often used where large diameter coils or high strength coils are desirable, e.g., in large vessel or aneurism occlusion.

The present invention includes combinations of substrates and fibers where the substrates are deployable using any of a variety of number of detachment devices. For instance, the invention includes substrates such as are taught in Guglielmi et al (U.S. Pat. No. 5,122,136 and its Continuation-in-Part U.S. Pat. No. 5,354,295); that is, substrates which are electrolytically detachable from the pusher or core wire used to advance the substrate through the delivery catheter to the selected delivery site. Mechanically detachable coils, such as those found in U.S. Pat. No. 5,261,916, to Engelson; in U.S. Pat. No. 5,304,195, to Twyford et al; in U.S. Pat. No. 5,312,415, to Palermo; in U.S. Pat. No. 5,350,397, to Palermo et al are all suitable for use as the substrate in this invention.

Other coils suitable as the substrate component 11 of the present invention include, but are not limited to coils having secondary shape characteristics, such as for example vortex or spiral secondary shape characteristics, (e.g., U.S. Pat. No. 4,994,069, to Ritchart et al) may be used as substrates for the present invention. Each of these patents is incorporated by reference.

The fibers of the invention may be a bundle of individual fibers or filaments (typically 5 to 100 fibers per bundle, preferably 20 to 30 fibers per bundle). The fibers 12 may be made of thermoplastic polymeric material or selected from materials such as Dacron (polyethylene terephthalate), polyolefins such as polyethylene and polypropylene, polyurethane, polyvinylchloride, vinylidenechloride, polyglycolic acid, polylactic acid, fluorocarbon polymers such as polytetrafluoroethylene, Nylons (polyamide), or silk. The length of fibers 12 can range from 0.5 mm to 100 mm, typically ranging from 1.0 mm to 5.0 mm.

In FIG. 2, the fibers 12 are as individual fibers or filaments that have separated from a bundle when introduced into substrate coil 11. The multiple separated fibers 12 are separated, as if by a comb, amongst the adjacent windings 14, 15 of the coil. The fibers act as spreaders between the coil turns when those turns are closely spaced. In this configuration, elastic recoil of the coil windings exert a force on the fibers 12 partially to hold them in place, although, perhaps obviously, such fibers may still be easily pulled and detached from said coil 11. This is particularly true when the coil substrate 11 has a secondary coil geometry as shown in Ritchart et al or is otherwise put on a bend radius. In such a situation, the outer radius side of the coil is open, increasing the spacing between windings. The elastic recoil forces of the coil windings onto the fibers can aid in creating a deformation 13 of fibers 12 during heating to help secure fibers 12 to coil 11 when heated.

Figure 3A:
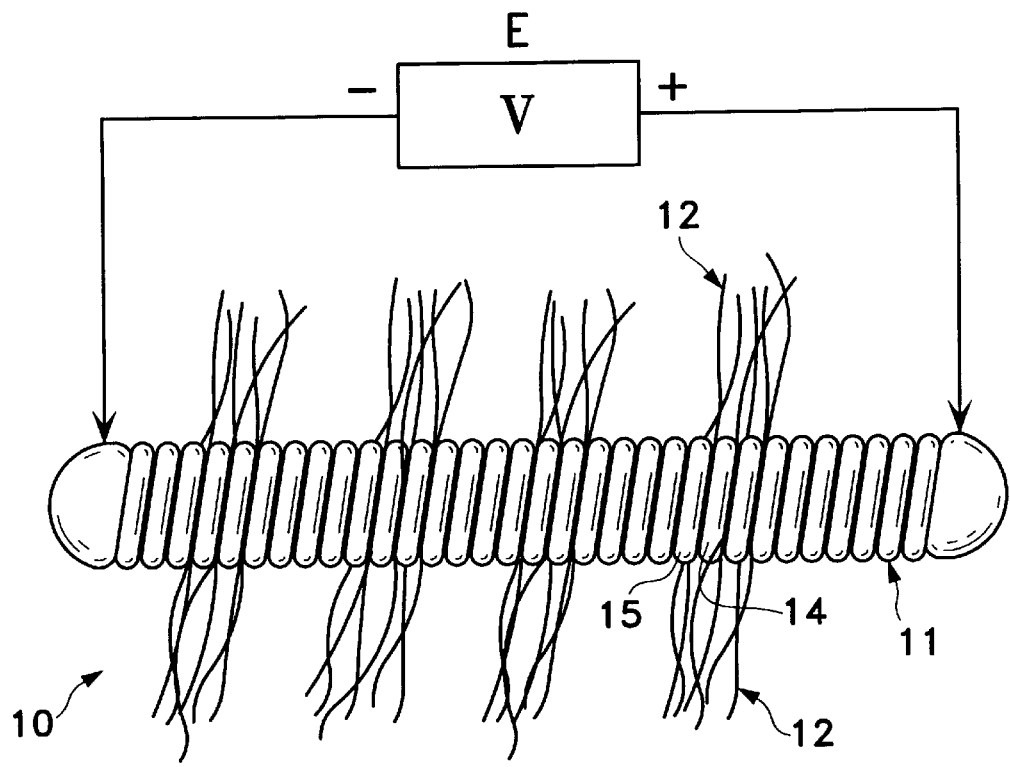
FIGS. 3A, 3B, and FIG. 4 show side views of representative configurations for preferred methods of making an occlusion device by heat securing fibers to a substrate.
Figure 3B:
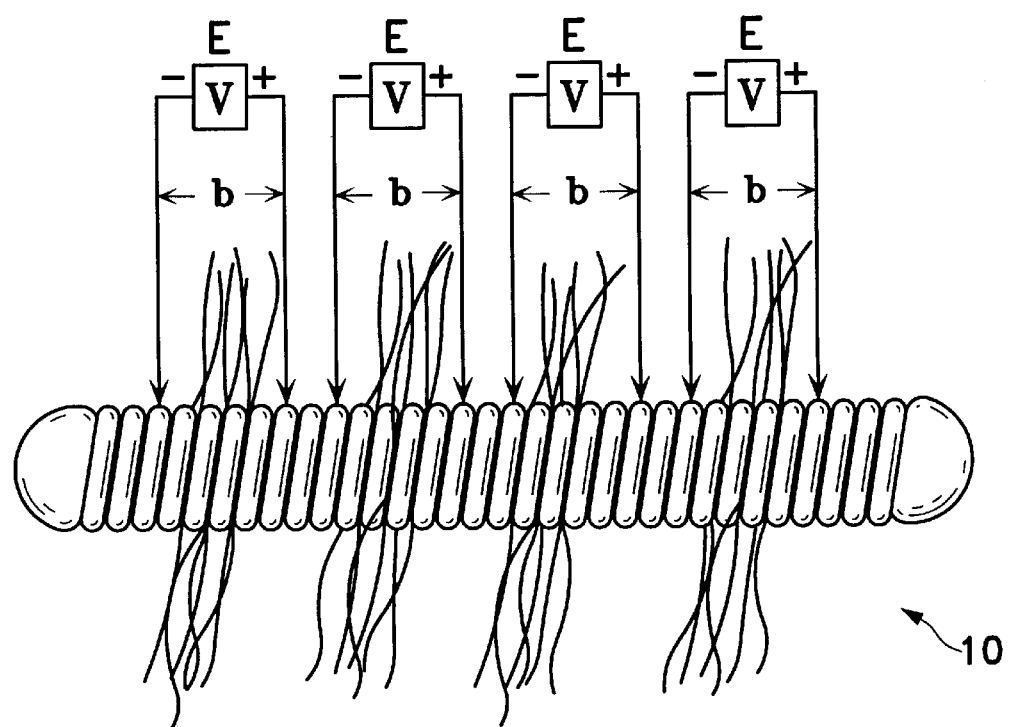
Figure 4:
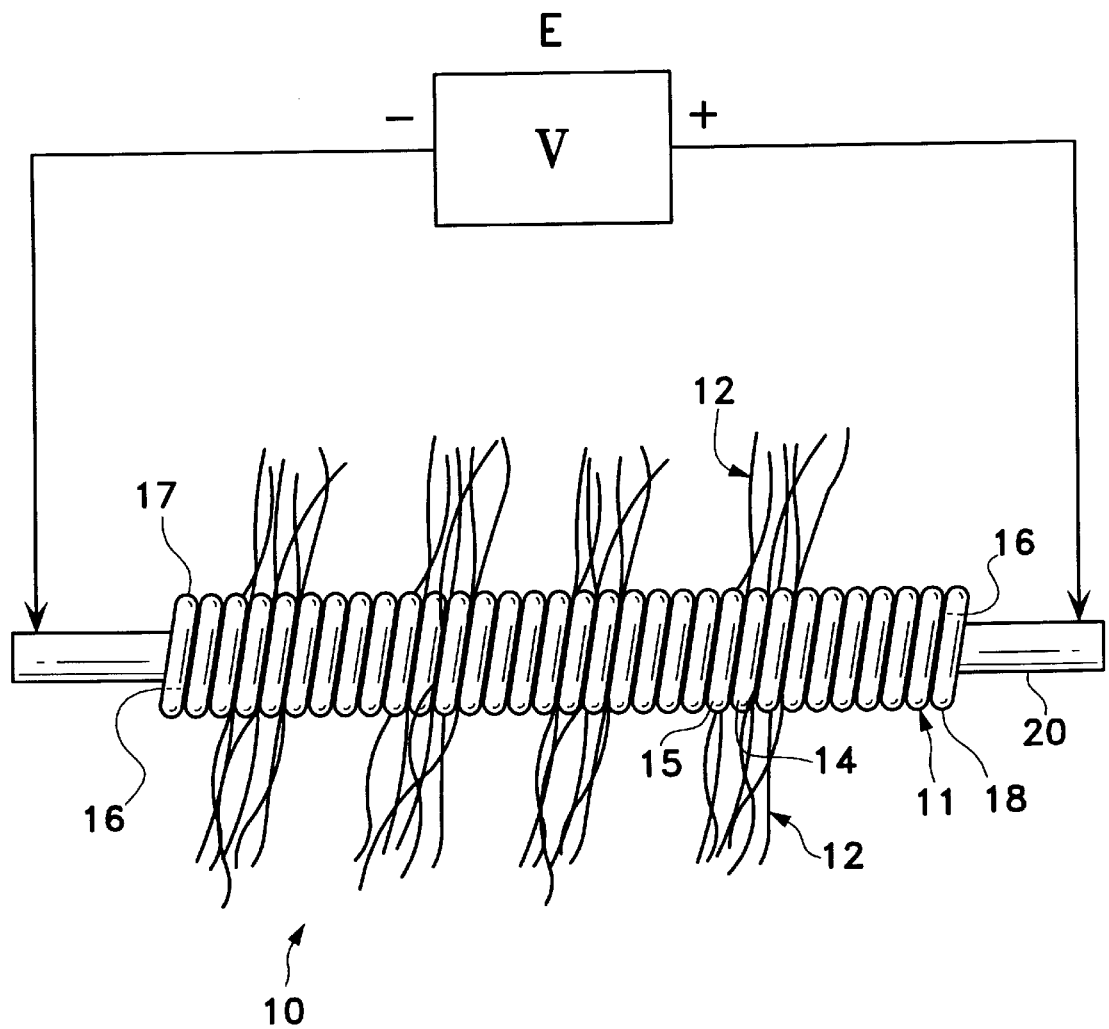

FIGS. 3A, 3B, and 4 show preferred ways to practice the inventive method of applying heat to deform either fibers or a substrate and secure the fibers to the substrate and form the inventive device. In the preferred methods described, the heat is localized in the region where the fibers meet the substrate. This procedure precludes deformation of the fibers that is unnecessary to the securement of the fibers. This localized heating allows retention of the benefit permitting the fibers to extend radially from the substrate for enhancing a thrombogenic or tissue in-growth response.

FIG. 3A shows a first preferred method of making the occlusive device 10 in FIG. 1. Using this method, substrate 11, itself, serves as the heat source for securing fibers 12 thereto. It is further preferred that substrate 11 comprises a metal coil wherein the coil is heated by using power source E to apply a voltage V across the coil and induce a current I therethrough, as shown here in FIG. 3A. This simple circuit causes the resistive metal in the substrate 11 to emit heat to deform the fibers 12.

It should be apparent from the description of the invention herein that although the resistant heat source in this procedure may be primarily a formed metal, other substrate materials suitable for producing the necessary heat include but are not limited to such materials and mixtures as: wire-imbedded or etched composites, laminates, metal hypotubes, or any other material that contains a conductive heat emitting element and performs functionally as a substrate adapted for placement within a body lumen or cavity.

A further embodiment of the first preferred method, shown in FIG. 3B, involves heating only the isolated regions of substrate coil 11 where a fiber or plurality of filament fibers 12 are introduced. In this method, a shorter distance of substrate, here shown as b, is heated at a given time, minimizing the effect of resistance variables that could otherwise significantly impact the current-induced heat production when applying a voltage over a significantly longer length of wound coil or other substrate.

Heating the substrate and fiber in the way shown in FIG. 3B results in localizing the produced heat within the lumen formed by the substrate coil 11 and at the substrate coil 11 surface.

FIG. 4 shows another preferred method of using heat to secure fibers 12 to substrate 11 (again shown here by example as a coil). Because of the variability in voltage/resistance/current/heat relationships of a long length of wound coil, this method is somewhat easier to practice consistently than the method discussed just above.

In this preferred method, a heat source 20 is extended into and through lumen 16 formed by substrate 11. This heat source 20 emits heat within lumen 16 to thereby cause the localized deformation of the fibers desirable for securing fibers 12 to substrate 11.

Preferably, heat source 20 is an electrically conductive elongate member. It is even more desirable that the heat source is in the form of a metal mandrel, perhaps used as the mandrel for winding and heat treating the substrate coil. Again, it is preferred that the fiber take the form of a thermoplastic polymer. Mandrel 20 is heated by using a power supply E to apply a voltage V across the mandrel or otherwise by causing current to flow therethrough. By heating the inside of substrate 11 with the mandrel, there is a temperature gradient between the lumen 16 of the coil and the exterior space surrounding coil 11 where the fibers 12 radially extend and terminate. This gradient is largely due both to temperature drop as a function of distance from heat source 20 and due to a heat sink role played by the substrate 11, particularly when it is in the form of a thermally conductive metal coil.

The resultant fiber deformation due to heating the substrate and coils with this method is also highly localized. Using the preferred materials for substrate (metal coil) and fiber (thermoplastic polymer, preferably Dacron), this localized deformation is largely present at the interior junction between the fiber element within the lumen of coil 11 and the interior surface of that coil 11.

The method depicted in FIG. 4 preferably uses a mandrel, which may be coated with a heat resistant covering, e.g., PTFE or the like, which resists adherance to the fiber material. The mandrel 20 may have an outer diameter ranging from 0.002 inch to 0.009 inch, preferably 0.004 inch, for use in a coil having a 0.009 inch inner diameter.

In carrying out the method shown in FIG. 4, fibers 12 are placed generally perpendicular to the long axis of coil 11 and between coil windings, such as shown at 14 and 15, at desired intervals along the length of the coil 11. Mandrel 20 is advanced through inner lumen 16 of coil 11 such that it extends beyond each end 17 and 18 of coil 11. A voltage V of approximately 2–3 Volts may be applied across a length of mandrel 20 subsuming the length of the coil lumen 16, resulting in an applied current of approximately 0.25–0.40 Amperes for a mandrel 20 of the given dimensions. The resultant current heats the mandrel and causes a deformation of portions of fibers 12 within the lumen of coil 11. Such deformation thereby secures fibers 12 to the coil 11 and prevent them from loosening when the mandrel 20 is withdrawn from coil 11 after the heat deformation process.

The procedures described above may also be performed with inductive heating, desirably localized, rather than resistive heating. Direct heat transfer, e.g., by radiation, may also be used to perform these procedures. Alternatively, a light source may be employed as the energy source either within or without the lumen of the substrate, to cause heating of the fiber or substrate and thereby secure the fiber to the substrate.

To the extent that any of these heat sources are appied in a non-localized manner, there are some detrimental side effects to their use. For instance, it may be difficult to prevent deformation or stiffening of the polymeric fibers or substrate when using less localized heat sources.

In any or all embodiments, the applied heat used to secure the fibers to the substrate may result in many differing chemical or mechanical mechanisms of securing the fibers 12 to substrate 11. Any such resultant mechanism is within the scope of the invention as long as such mechanism results from heating the interface of substrate and fibers to secure them together for use as a device for occluding body lumens or cavities.

Figure 5:
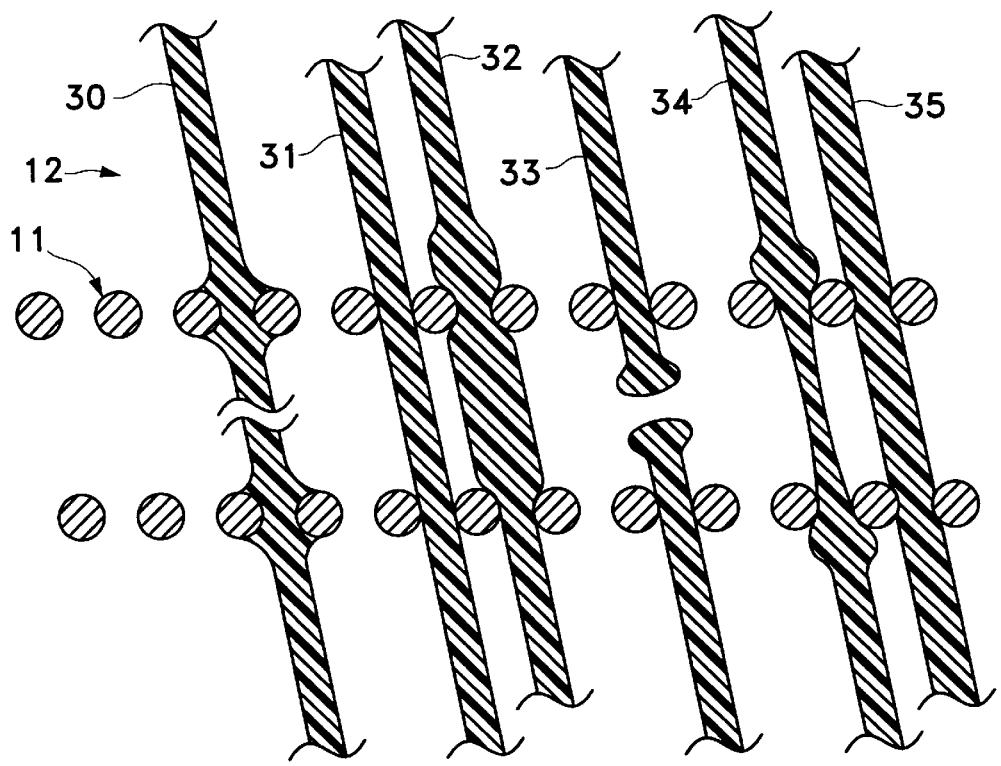
FIG. 5 and FIG. 6 show a partial cross sectional side view and end view, respectively, of preferred orientations of secured fibers relative to the substrate.

FIG. 5 provides some examples, non-inclusive of all possible mechanisms, of fiber deformations and related mechanisms resulting in securing the fibers to a substrate coil in the present invention.

For instance, the heat source may be of sufficient temperature to melt the fiber or substrate, thereby securing the fiber to the surface of substrate coil (once melted and then cooled) as is shown at representative fiber 30 of FIG. 5. Preferably, the fiber is made of Dacron, having a melting point of 250–350° F.

It is possible to achieve fusion of the component materials of the fiber and substrate if at least a portion of the substrate and at least a portion of the fiber are of the same or similar material such that each has a melting response to the applied heat. Such would be the case, for example, where a polymer is co-extruded onto the metal wire forming the coil, said polymer being of similar properties to a polymer material of the fiber, both of the polymers melting together to form a melt bond.

Fibers may also be mechanically secured at the interface with the substrate due to a deformation of either the fiber or the substrate due to heating. In such a case, there is a deforming of the substrate or fibers, either alone or in addition to melting the substrate or fibers, that mechanically secures these components together. Preferably, such deformation would be in thermoplastic polymeric fibers and the substrate again would be a metal coil.

Mechanically securing the fibers to the substrate, as contemplated by the present invention, includes fibers melting or merely softening under elevated heat and deforming at the interface with the substrate coil, conforming their geometry to the unsoftened substrate surface at the interface and remaining so conformed in the deformed geometry after cooling. Although this described "mechanically conformed" configuration appears similar to the melted fiber configuration shown in representative fiber 30 of FIG. 5, here the geometric conformity is what mechanically prevents detachment, as opposed to "melting" as the term is used in this text to mean both the state change in the material as well as the surface interaction securing a first material to another when it is "melted" to it.

The fibers may also simply deform into a new shape after a heating step that effectively prevents the fibers from being withdrawn from the substrate. In such a case, the fiber is removeably interlaced with the coil before heating, such as when threaded between windings of the coil with the long axis of the fibers substantially in parallel alignment with the windings, shown by example in representative fiber 31 of FIG. 5. The deformed shape of the fiber after heating subsequently prevents it from being removed through said windings, such as where the deformed geometry of the fibers in the coil lumen has a dimension that will not easily fit through the winding spacing, as is shown in representative fibers 32, 33, 34, and 35 of FIG. 5.

Such a configuration may be achieved, for example, by irradiating fibers made of polymeric material to create a cross-linked recovery memory diameter, subsequently necking the fibers down to a smaller diameter, threading the fibers through the coils, and then heating the fibers. This would cause the fiber to recover to a larger dimension in the lumen, and perhaps in the exterior space closely surrounding the coil, a dimension equal to or less than the recovery memory diameter but greater than the necked diameter. The coil windings restrict such recovery in the space therebetween, with the larger recovered sections being required to fit through the spacing between the coils in order to un-thread the fiber from the coil. This is shown in representative fiber 32 of FIG. 5.

Another way such a deformation for securing fibers to substrate may be achieved, for example, is by the simple amassing of the deformed fibers when melted, so that the amassed portions have geometry that can not fit between the winding spacings to be pulled therethrough for removal of the fiber. An example of this is shown in representative fiber 33 of FIG. 5. This is a mechanism in contrast with melting the fiber onto the coil, such as in representative fiber 30 of FIG. 5, wherein there is a resultant surface interface between fiber and coil to prevent detachment. Fiber 33 shows, for purpose of example only, that the middle portion of the fiber may become so deformed as a result of the local heating that a break in the continuity of the fiber occurs. The sides of the fiber, formed after breaking, are still considered as the same fiber.

Representative fiber 34 shows an example of a fiber being deformed both within the lumen of the coil and in the exterior of the coil, but closely surrounding the coil. Such a configuration is also a result of heating that would effectively secure the fiber to the coil, as the fiber could not be threaded back through and away from the coil.

Representative fiber 35 shows an example of a fiber softening or melting while the elastic recoil force of the coil windings pinch into the softened or melted fiber to embed the windings into a deformed state, thereby securing the fibers to the coils.

Other embodiments of the invention include fibers each having end portions extending from the substrate substantially spaced from the other radially about the substrate, desirably at generally equal lengths. Preferably, the end portions of the fibers extend outwardly from the substrate coil at least 90° radial separation from each other. This is repeatably achieved by the method of the invention described in various embodiments described above.

Figure 6:
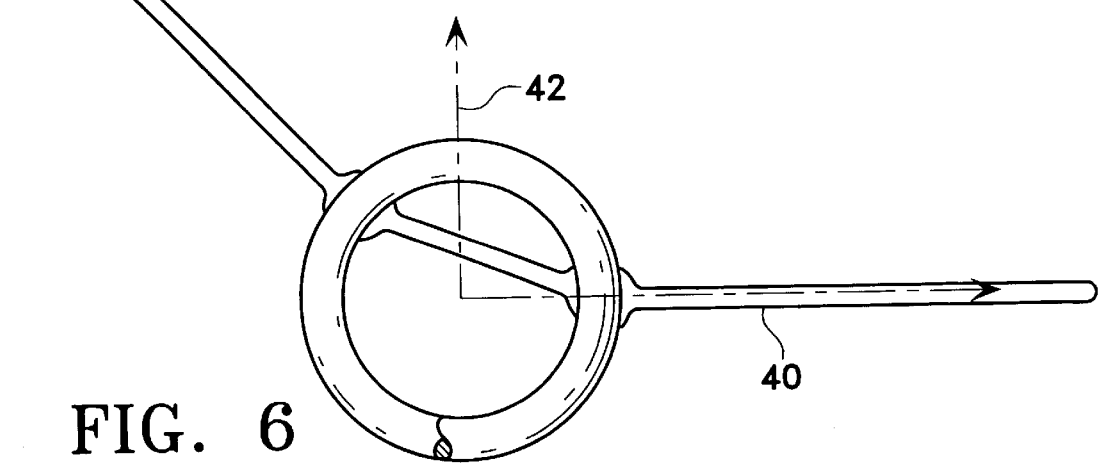

FIG. 6 shows representative fiber 40 in the described orientations which, either taken separately or when taken together, are designed to reduce friction during co-axial delivery through conduit sheaths or tubes as well as to achieve desired thrombogenic or other tissue in-growth responses. The orientation angle 42 mentioned above is shown in FIG. 6.

The vasoocclusion device of this invention may be used in a preferred manner similar to the procedure shown in U.S. Pat. No. 4,994,069. Briefly, the coil may be supplied in prepackaged form in a sterile cannula which is adapted to engage the proximal end of a catheter. The fiber end portions will be pressed flat against the coil for placement in the cannula and catheter.

Once the catheter is in place within the vessel, the coil-containing cannula is placed into engagement with the proximal end of the catheter and the coil is transferred from the cannula lumen into the catheter lumen by exerting force on the proximal end of the coil. A pusher rod is used to push the coil through the catheter to the desired coil release site. While tracking through the co-axial luminal space, the free fiber ends of the invention naturally groom themselves in a linear orientation parallel with the direction of travel, a desired configuration for reducing resistance from the plane of friction at the inner lumen surface of the delivery catheter. Fibers having ends radially separated on substantially opposite sides of the coil will also minimize frictional resistance, spreading the distribution of such resistance into a more evenly distributed load component about the radial axis.

The location of the coil may be visualized due to the radiopacity of the helical coil. Once at the site, the coil is plunged from the catheter lumen into the vessel. This allows the flexible fiber ends to extend outwardly from the coil surface to fill the vessel.

Modifications of the above-described modes for carrying out the invention that are obvious to those of skill in medical device design generally, and vasoocclusion specifically are intended to be within the scope of the following claims.

We claim as our invention:

1. A method for making a device for occluding a lumen or cavity in a mammal, comprising the steps of:
   (a) bringing fibers into contact with a substrate to form an interface therebetween; and
   (b) causing the substrate to emit heat so the fibers at the interface are secured to the substrate.

2. The method of claim 1, wherein the substrate comprises a heat source, and wherein heating step (b) comprises emitting heat from the heat source, causing a deformation at the interface to secure the fibers to the substrate.

3. The method of claim 1, wherein the substrate is an electrically conductive coil, and wherein step (b) further comprises causing an electrical current to flow through the coil.

4. The method of claim 1, wherein the substrate defines an inner lumen, and wherein step (b) comprises extending a heat source into the lumen and then emitting heat from the heat source, causing a deformation at the interface to secure the fibers to the substrate.

5. The method of claim 4, wherein the heat source comprises an electrically conductive member and wherein step (b) further comprises causing an electrical current to flow through the member.

6. The method of claim 1, wherein step (b) comprises melting at least one of either the substrate or the fibers to secure the fibers to the substrate at the interface.

* * * * *